US011610022B2

(12) United States Patent
Hennessy et al.

(10) Patent No.: US 11,610,022 B2
(45) Date of Patent: Mar. 21, 2023

(54) PRIVACY PRESERVING PERSONAL HEALTH RECORD SERVICE ECOSYSTEM TRIALS

(71) Applicant: KONINKLIJKE PHILIPS N.V., Eindhoven (NL)

(72) Inventors: Mark Anthony Hennessy, Eindhoven (NL); Murtaza Bulut, Eindhoven (NL); Mark Thomas Johnson, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 261 days.

(21) Appl. No.: 16/904,636

(22) Filed: Jun. 18, 2020

(65) Prior Publication Data
US 2020/0401727 A1    Dec. 24, 2020

Related U.S. Application Data

(60) Provisional application No. 62/864,617, filed on Jun. 21, 2019.

(51) Int. Cl.
*H04L 9/32*     (2006.01)
*G16H 10/60*    (2018.01)
*G06F 21/62*    (2013.01)
*G06F 21/33*    (2013.01)

(52) U.S. Cl.
CPC .......... *G06F 21/6254* (2013.01); *G06F 21/33* (2013.01); *G16H 10/60* (2018.01); *H04L 9/3213* (2013.01)

(58) Field of Classification Search
CPC .. G06F 21/6254; G06F 21/33; G06F 21/6245; G16H 10/60; H04L 9/3213; H04L 2209/80; H04L 9/3239
See application file for complete search history.

(56) References Cited

U.S. PATENT DOCUMENTS

| | | | | |
|---|---|---|---|---|
| 7,424,617 | B2 * | 9/2008 | Boyd ................. | G06Q 30/0226 463/16 |
| 2013/0132854 | A1 * | 5/2013 | Raleigh ................. | H04M 15/77 715/738 |
| 2014/0344435 | A1 * | 11/2014 | Mortimore, Jr. ........ | H04L 43/50 709/223 |
| 2015/0332283 | A1 | 11/2015 | Witchey | |

(Continued)

OTHER PUBLICATIONS

Wikipedia contributors. (May 18, 2018) Distributed ledger. In Wikipedia, The Free Encyclopedia. Retrieved 10:27, May 21, 2018, from https://en.wikipedia.org/w/index.php?title=Distributed ledger &oldid=841869633.

(Continued)

*Primary Examiner* — Catherine Thiaw
*Assistant Examiner* — Andrew Suh

(57) ABSTRACT

A user device comprises an app that stores and maintains exclusive control of user data, and causes one or more processors to send a request for services according to a trial period to a distributed ledger associated with service providers and anonymously interact with the service providers according to a set of rules maintained in the distributed ledger by passing along a token uniquely associated with the user during for the respective interaction with each service provider without the user data being shared with the service providers.

20 Claims, 8 Drawing Sheets

(56) References Cited

U.S. PATENT DOCUMENTS

| | | |
|---|---|---|
| 2017/0140101 A1 | 5/2017 | Anderson et al. |
| 2017/0161439 A1* | 6/2017 | Raduchel ............ H04W 12/033 |
| 2018/0117446 A1 | 5/2018 | Tran et al. |
| 2019/0172566 A1 | 6/2019 | Chander et al. |
| 2019/0236598 A1* | 8/2019 | Padmanabhan ........ G06N 20/00 |

OTHER PUBLICATIONS

Wikipedia contributors. (Apr. 11, 2018) Proof-of-work system. In Wikipedia, The Free Encyclopedia. Retrieved 10:30, May 21, 2018, from https://en.wikipedia.org/w/index.php?title=Proof-of-work_system&oldid=835940703.

Wikipedia contributors. (May 20, 2018). Proof-of-stake. In Wikipedia, The Free Encyclopedia. Retrieved 10:29, May 21, 2018, from https://en.wikipedia.org/w/index.php?title=Proof-of-stake&oldid=842086874.

Wikipedia contributors. (May 17, 2018) Byzantine fault tolerance. In Wikipedia, The Free Encyclopedia. Retrieved 10:40, May 21, 2018.

Wikipedia contributors. (Apr. 16, 2018) Personal health record. In Wikipedia, The Free Encyclopedia. Retrieved 11:14 May 21, 2018, from https://en.wikipedia.org/w/index.php?title=Personal_health_record&oldid=836776277.

* cited by examiner

PRIVACY PRESERVING PERSONAL HEALTH RECORD SERVICE ECOSYSTEM TRIALS

FIELD OF THE INVENTION

The present invention is generally related to data privacy, and more particularly, privacy in personal health record services.

BACKGROUND OF THE INVENTION

A Personal Health Record (PHR) is a health record where health data and information related to the care of a person is maintained by his or herself (hereinafter, using the male pronoun with the understanding that both genders may apply). A PHR may be viewed as a system of records for the health of the person, and includes data sharing controls regarding with whom the data is shared. The kinds of data stored in a PHR is quite broad, and includes information about their allergies, adverse drug reactions, family medical history, any chronic diseases, illnesses and hospitalizations, lab results, imaging reports (e.g. X-Rays, CT scans etc.), prescription records, medications and dosages, vaccinations, surgeries, observations of daily living, and/or any personally collected health data from health data sources (e.g., personal health devices, social media sources, etc.).

From an architectural point of view, a PHR may be perceived as a storage and access control layer, where the data format/semantics of patient data is normalized. Then, applications can be built on top of this storage layer. In practice of course, there needs to be a large infrastructure behind the PHR, as connectivity to the electronic health records (EHRs) of health care providers is needed to populate the PHR with up-to-date health data of the patient such that those data sources can be trusted, and the provenance of the data is maintained. Stakeholders who may have an interest in a PHR include the patient themselves, healthcare providers wanting to provide safer healthcare, and/or insurance companies whom want to have an accurate view of how the patient is being treated to be able to verify insurance claims.

Today there are many services built around using and processing PHRs, where user data is collected and used for various purposes. For instance, during sign-up, users are usually asked to provide sensitive personal information and their data is collected when using the service. However, later, when the user unsubscribes or stops using the service, completely deleting one's user data from the service providers' records is not straightforward (or maybe it is not possible at all). The risk of not being able to manage one's data, if a service turns out to be undesirable, deters users from signing up for personal health record services.

SUMMARY OF THE INVENTION

One object of the present invention is to ensure the privacy of user data while permitting exclusively user control towards any access by a third party to the user data. To better address such concerns, in a first aspect of the invention, a user device is disclosed that comprises an app that stores and maintains exclusive control of access of user data, and causes one or more processors to send a request for services according to a trial period to a distributed ledger associated with service providers and anonymously (e.g., the user and/or user data remains anonymous) interact with the service providers according to a set of rules maintained in the distributed ledger by (automatically) passing along a token uniquely associated with the user during the respective interaction with each service provider without the user data being shared with the service providers. By controlling interactions through the distributed ledger while maintaining local control of the user data, a user is able to keep better control of their personal data while also facilitating the ability for the user to move back and forth between trial services to determine their provider preference. Also, one or more benefits accrue to the service providers, since each provider is able to track the duration of use of each respective trial period services, providing confidence that the trial period services are administered fairly.

In one embodiment, the user device generates the token based on a combination of characteristics of the user device and a unique self-sovereign identity. The self-sovereign identity enables the user to store their own identity data on their own devices and provide it efficiently to those who need to validate it, without relying on a central repository of identity data.

In one embodiment, wherein the set of rules correspond to a trial duration offer for each of the service providers. By monitoring the trial duration offer, the service providers are ensured that the trial period services are offered on a fair basis.

In one embodiment, the set of rules prevents a transfer of the token and interactions with the trial period services is terminated. The user is thus in control of whether the token is transferred to another service provider. If the user decides he or she does not wish to continue the trial period, at most the user may lose incentives.

In one embodiment, the user device communicates a first subscription to one of the service providers after completion of the plural trial period services and a second subscription with another of the service providers after interacting with the one of the service providers according to the first subscription, the user device controlling the sharing of the user data between the one of the service providers and the another of the service providers. Thus, after the trial period and upon selection of a subscription, the user may control the sharing of any user data provided according to the selected subscription if he or she chooses to subscribe to another one of the service providers.

In one embodiment, the user device switches among the plural trial period services before completing a prescribed trial period duration in each trial period service as long as a total duration prescribed for each of the trial period services has been met. By permitting the user to jump from one service provider to another at will, the user may be afforded more flexibility while the service providers are ensured of equal treatment.

In one embodiment, the trial period services correspond to personal health record services. In the burgeoning business of third party PHR services, the ability to preserve user data privacy while providing service providers with a fair and monitorable trial period fosters more acceptance of PHRs among patients, which benefits the patient care.

These and other aspects of the invention will be apparent from and elucidated with reference to the embodiment(s) described hereinafter.

BRIEF DESCRIPTION OF THE DRAWINGS

Many aspects of the invention can be better understood with reference to the following drawings, which are diagrammatic. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION OF EMBODIMENTS

Figure 1:
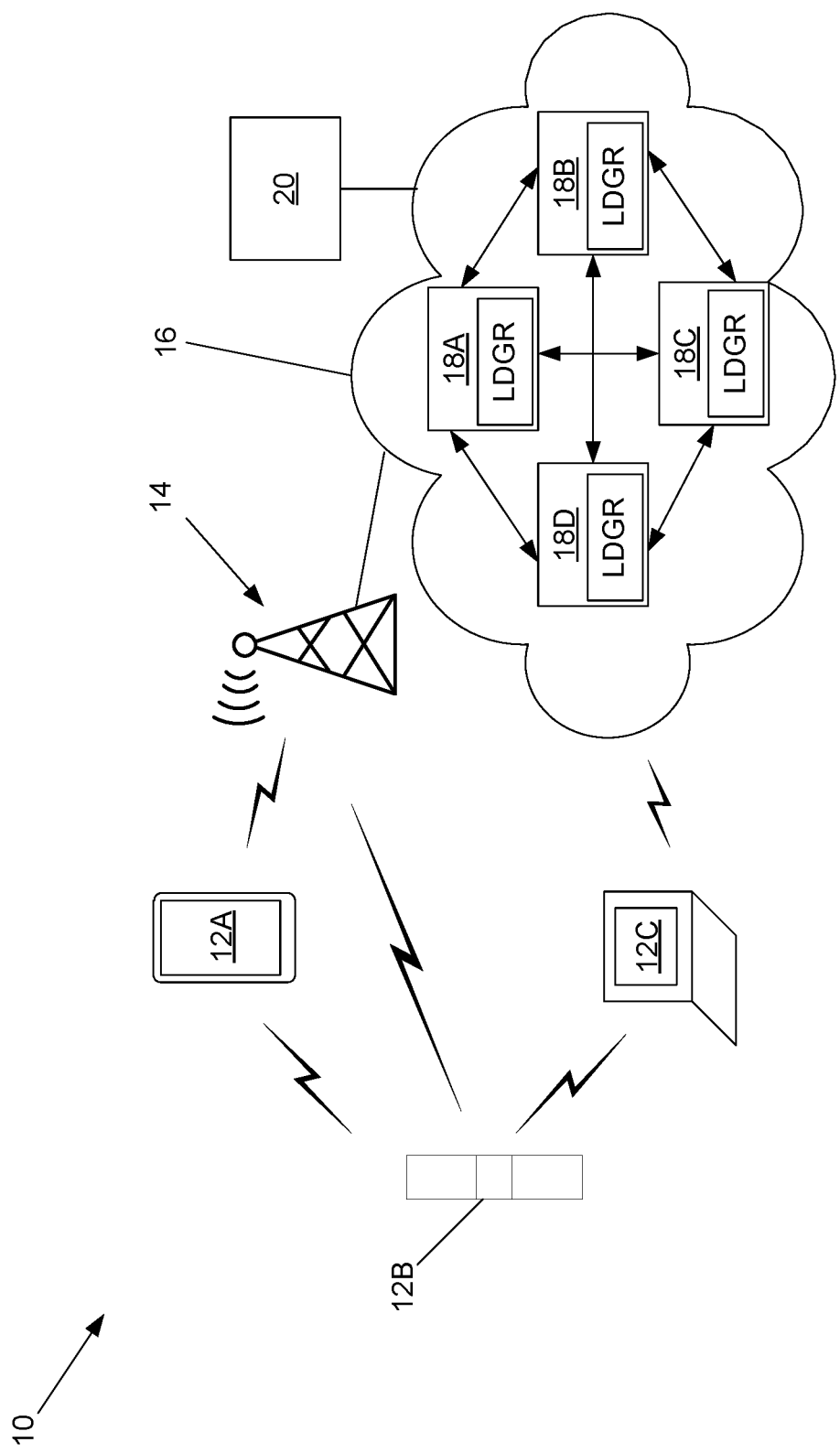
FIG. 1 is a schematic diagram that illustrates an example environment in which a personal health record (PHR) ecosystem is used, in accordance with an embodiment of the invention.

Disclosed herein are certain embodiments of a personal health record (PHR) ecosystem and method (collectively hereinafter referred to as PHR ecosystem) that comprises functionality to overcome the lack of control over user health data by implementing a distributed ledger solution that provides an option of operating a trial period in privacy within an ecosystem of competing PHR (third party) solutions. In one embodiment, the PHR ecosystem comprises a user device that includes a secure mobile app container that prevents user data from being sent out from the user device, the user device interacting in one embodiment over a peer-to-peer network of plural computing devices (e.g., nodes) that maintain and update a blockchain (e.g., a distributed ledger). The distributed ledger comprises a set of rules (a smart contract) that enforces trial period services per PHR ecosystem member (e.g., PHR service provider) and operates as a level of logic indirection to preserve anonymity between the PHR ecosystem and the user.

Digressing briefly, there are presently many services available that are built around using and processing PHRs. During sign-up, users are usually asked to provide sensitive personal information and their data is collected when using the service. Later, when the user unsubscribes or stops using the service, completely deleting one's user data from the service providers' records is not straightforward (or maybe it is not possible at all). The risk of not being able to manage one's data, if a service turns out to be undesirable, deters users from signing up for personal health record services. Also, service providers likewise have concerns with trial periods, since instances occur where trial periods are taken advantage of due to unsuitable methods to monitor trial periods of individual users. Through use of certain embodiments of a PHR ecosystem, user data is preserved and under exclusive control of the user, while service providers learn useful information (e.g., what services are of interest to a user) in a competing peer-to-peer network of PHR service providers.

Having summarized certain features of a PHR ecosystem of the present disclosure, reference will now be made in detail to the description of a PHR ecosystem as illustrated in the drawings. While a PHR ecosystem will be described in connection with these drawings, there is no intent to limit it to the embodiment or embodiments disclosed herein. For instance, emphasis is placed on PHRs, though in some embodiments, a trial ecosystem for trial periods for other defined types of services (e.g., other than PHR services) may be used and hence are contemplated to be within the scope of the disclosure. Also, though emphasis is on implementations where the nodes or computing devices are connected to each other in a network, in some embodiments, the computing devices may not be connected to each other in a network. Further, although the description identifies or describes specifics of one or more embodiments, such specifics are not necessarily part of every embodiment, nor are all of any various stated advantages necessarily associated with a single embodiment. On the contrary, the intent is to cover all alternatives, modifications and equivalents included within the principles and scope of the disclosure as defined by the appended claims. For instance, two or more embodiments may be interchanged or combined in any combination. Further, it should be appreciated in the context of the present disclosure that the claims are not necessarily limited to the particular embodiments set out in the description.

Note that reference to a trial period generally refers to the entire trial period that collectively includes the trial period services provided by a service provider. In other words, a trial period is comprised of a plurality of mini-trial periods where the user interacts with the trial services provided by respective service providers, these mini trial periods engaged in by the plural service providers referred to herein as trial period services to contrast with the entire trial period.

Referring now to FIG. 1, shown is an example environment 10 in which certain embodiments of a PHR ecosystem may be implemented. It should be appreciated by one having ordinary skill in the art in the context of the present disclosure that the environment 10 is one example among many, and that some embodiments of a PHR ecosystem may be used in environments with fewer, greater, and/or different components than those depicted in FIG. 1. The PHR ecosystem may comprise all of the devices depicted in FIG. 1 in one embodiment, or a subset of the depicted devices in some embodiments. The environment 10 comprises a plurality of devices that enable communication of information throughout one or more networks. The depicted environment 10 comprises one or more user devices 12 (e.g., 12A, 12B, and 12C), a wireless/cellular network 14, and a network 16, which may include plural computing devices 18 (e.g., 18A, 18B, 18C, 18D, etc.) communicatively coupled to each other and to the user devices 12 and to a third-party device, including an oracle device 20. In one embodiment, the network 16 comprises a distributed ledger network (e.g., a peer-to-peer blockchain network), which comprises a decentralized network of computing devices or nodes that each comprises a copy of a ledger. The network 16 may further include one or more additional networks, including a wide area network (WAN), metropolitan area network (MAN), one or more local area networks (LANs), among other networks and/or data structures. Though the computing devices 18 are depicted as connected to each other (e.g., network-connected), in some embodiments, the computing devices 18 may not be connected to each other.

The user devices 12 comprise one of a plurality of types of devices, including a smartphone 12A, wearable device or activity tracker 12B, laptop computer 12C, among others (e.g., notebook, notepad, personal digital assistant, pager, Internet of things (IoT) devices (e.g., appliances, automotive devices, etc.), devices based on virtual or augmented reality technology (e.g., headsets), etc.). Though emphasis below is on the smartphone 12A, wearable device 12B, and laptop computer 12C, it should be appreciated that the user devices 12 contemplated within this disclosure include other or additional devices. For instance, data may be collected by professional user devices, which include wearable or non-wearable devices operated by a trained professional. Such professional user devices may include devices found in a medical facility (e.g., in a hospital or a therapeutic or rehabilitation facility to render therapy and/or monitor a user) and devices used at home (e.g., that may require training or instruction for home use, including blood test kits for children). The smartphone 12A may be in communications with the wearable device 12B and/or one or more computing devices 18 of the network 16. The smartphone 12A may include sensing functionality, including motion (e.g., acceleration), PPG, and/or ECG sensing. In one embodiment, the smartphone 12A comprises heart and/or breathing rate monitoring using a Philips Vital Signs Camera, or similar functioning devices from other manufacturers, to remotely measure heart and breathing rates using a standard, infrared (IR) based camera by sensing changes in skin color and body movement (e.g., chest movement)), among others. ECG measurements may be achieved using electrodes on, for instance, the casing of the smartphone 12A. In some embodiments, the smartphone 12A comprises an accelerometer, gyroscope, and location sensing functionality including a global navigation satellite system (GNSS) receiver, including a global positioning system (GPS) receiver, which tracks and provides location coordinates (e.g., latitude, longitude, altitude) for the device 12A. The smartphone 12A may further include one or more interfaces for providing feedback of a monitored condition and/or activity, including a display screen (e.g., touch-type) to provide health data monitored, or accessed by, the smartphone 12A. The smartphone 12A comprises wireless/cellular communication functionality, including cellular, streaming and/or broadband (e.g., 3G, 4G, 5G, LoRa, etc.), Wi-Fi, Blue-tooth, NFC, etc., which may be used for the communication of sensing data (e.g., health data), other user data, and/or feedback information among the devices 12 and/or the computing devices 18 of the network 16.

The wearable device 12B is typically worn by the user (e.g., around the wrist or torso, as a patch, or attached to an article of clothing, or even embedded within a user), and comprises a plurality of sensors that track motion and/or physical activity of the user (e.g., steps, swim strokes, pedaling strokes, limb movement, etc.), activity type (walking, cycling, running, etc.) and is further configured to sense/measure or derive physiological parameters (e.g., heart rate, average heart rate, resting heart rate, inter-beat intervals, blood pressure, pulse rate, respiration, skin temperature, etc.) based on the sensor data, and optionally sense various other parameters (e.g., context, including outdoor temperature, humidity, location, etc.) pertaining to the surrounding environment of the wearable device 12B. In one embodiment, the wearable device 12B comprises an electrocardiographic (ECG) sensor and a photoplethysmographic (PPG) sensor and an accelerometer and/or gyroscope. In some embodiments, the wearable device 12B may comprise a GNSS receiver, including a global positioning system (GPS) receiver, which tracks and provides location coordinates (e.g., latitude, longitude, altitude) for the device 12B.

Data collected by the one or more sensors of the wearable device 12B may be communicated to the user via an interface (e.g., an integrated display) on the wearable device 12B. In one embodiment, the wearable device 12B uses the integrated display to also provide feedback to the user of a monitored condition and/or activity (e.g., health data). Such data collected by the wearable device 12B may be communicated to the smartphone 12A, the laptop 12C, and/or to other devices coupled to the network 16. Communication functionality of the wearable device 12B includes wireless functionality (e.g., near field communications (NFC), Blue-tooth, 802.11-based technology, streaming technology, including LoRa, and/or broadband technology including 3G, 4G, 5G, etc.) and/or wired functionality (e.g., via universal serial bus (USB), etc.).

The laptop 12C comprises typical data processing functionality, and communication functionality includes wireless communications (e.g., NFC, Blue-tooth, 802.11-based technology, streaming technology, including LoRa, and/or broadband technology including 3G, 4G, 5G, etc.) and wired functionality (e.g., USB, Ethernet, etc.) to receive (e.g., from the network 16 and/or the device 12B) health data and/or other user data.

One or more of the user devices 12 may include middleware (e.g., web services interfaces or web application programming interfaces (APIs) (e.g., SOAP, HTTP, XML, etc.), other APIs, etc.) that enable access to remote computing devices (e.g., to access electronic health records and/or other health data). For instance, cooperation between the user devices 12 and devices of the network 16 may be facilitated (or enabled) through the use of one or more remote procedure calls (RPCs) or generally APIs that may define one or more parameters that are passed between a calling application and other software code such as an operating system, library routine, function that provides a service, that provides data, or that performs an operation or a computation. The API may be implemented as one or more calls in program code that send or receive one or more parameters through a parameter list or other structure based on a call convention defined in an API specification document. A parameter may be a constant, a key, a data structure, an object, an object class, a variable, a data type, a pointer, an array, a list, or another call. API calls and parameters may be implemented in any programming language. The programming language may define the vocabulary and calling convention that a programmer employs to access functions supporting the API. In some implementations, an API call may report to an application the capabilities of a device running the application, including input capability, output capability, processing capability, power capability, and communications capability.

In one embodiment of a PHR ecosystem, one or more of the user devices 12 store PHRs according to a self-sovereign identity approach, where persons associated with the user devices 12 store their own identity data on their own devices, and provide it efficiently to those who need to validate it, without relying on a central repository of identity data. For instance, the one or more user devices 12 may comprise a secure PHR storage that is under full (exclusive) control of the user, enabling the user to decide what health data may be accessed and for what purpose. As is described further below, one or more of the user devices 12 comprise a mobile app that is capable of running other containerized applications inside of it, enabling a respective user to store user-controlled, PHR data (e.g., in the secure PHR storage) independent of third party PHR service providers. That is, in one embodiment of a PHR ecosystem for PHR trial period services provided by PHR service providers, one or more of the user devices 12 include a PHR ecosystem trial app that runs a secure mobile app container and runs on the user device(s) 12. The secure mobile app container prevents user data from being sent out from the user device 12. The PHR ecosystem trial app provides the ability to securely install, execute, and vacate a PHR application as the trial process is orchestrated. The PHR ecosystem trial app also provides a capability to interact with a distributed ledger to generate the ecosystem trial preferences specified by the user, as described further below.

Digressing briefly, there are generally three parts to identity: claims, proofs, and attestations. An identity claim is an assertion made by the person or business (e.g., my name is Mr. Jones and my date of birth is Jan. 4, 1972). A proof is some form of document that provides evidence for the claim. Proofs come in all sorts of formats. Usually for individuals it includes photocopies of passports, birth certificates, and utility bills. For companies, it may include a bundle of incorporation and ownership structure documents. An attestation is when an authority or third ($3^{rd}$) party validates that according to their records, the claims are true (e.g., a university may attest to the fact that someone matriculated there and earned a degree). An attestation from the proper authority is more robust than a proof, which may be forged. However, attestations are a burden on the authority as the information can be sensitive. This means that the information needs to be maintained so that only specific people can access it.

The wireless/cellular network 14 may include the necessary infrastructure to enable wireless and/or cellular communications between the user devices 12 and one or more devices of the network 16. There area number of different digital cellular technologies suitable for use in the wireless/cellular network 14, including: 3G, 4G, 5G, GSM, GPRS, CDMAOne, CDMA2000, Evolution-Data Optimized (EV-DO), EDGE, Universal Mobile Telecommunications System (UMTS). Digital Enhanced Cordless Telecommunications (DECT), Digital AMPS (IS-136/TDMA), and Integrated Digital Enhanced Network (iDEN), among others, as well as Wireless-Fidelity (Wi-Fi), 802.11, streaming, for some example wireless technologies.

The network 16 is depicted as a peer-to-peer (decentralized), blockchain or generally, distributed ledger network, though it should be appreciated that the network 16 may comprise additional types of networks in some embodiments, as described above. In one embodiment, the computing devices 18 or nodes record, share and synchronize transactions in theft respective electronic ledgers (LDGRS), rather than keeping data centralized as in a traditional ledger. Each copy of the ledger is updated based on the rules in the smart contract. The smart contract is validated as being the same on each node and logic is executed in each node. There is consensus when the results agree. In general, distributed ledgers are the building blocks of "internet of value," and enable recording of interactions and transfer value in a peer-to-peer manner, without a need for a centrally coordinating entity or trusted 3rd party. Value refers to any record of ownership of an asset—for example, money, securities, land titles—and also ownership of specific information like identity, health information and other personal data. In one embodiment, each of the computing devices 18 may correspond to a respective service provider for PHP services. A distributed ledger organizes timestamped transactions and data into blocks; which are chained together in an append only mode. The creator of a block is decided upon using a distributed consensus algorithm. There are different kinds of consensus algorithms, with their aim to order the transactions in the block. The ledger may be public or private or some combination thereof, which in turn dictates the manner in which the distributed consensus is applied. For example, in a public/permissionless system where any party can write to the ledger, a Proof-of-Work (PoW) technique may be used, Proof-of-Stake (PoS) is another consensus approach which may be used in a permissionless distributed ledger context for reaching consensus. In this case PoS involves each participant taking a financial stake in the system to have the authority to write transactions. One aim of all of these distributed consensus algorithms is to implement some level of Byzantine Fault Tolerance, (BFT), where the system is capable of reaching consensus even when there are some faulty or bad actors in the system. In some embodiments, the service providers associated with the computing devices 18 may wish to maintain confidential transactions between each other, in which case a distributed ledger can maintain different ledgers configured to only be accessed by those authorized to access it.

In one embodiment, the network 16 provides a blockchain for trusted logging of transactions for all ecosystem stakeholders (e.g., third party or PHR service providers) to check or monitor the integrity of an application running (e.g., the PHR ecosystem trial app) any of the user devices 12 for the purpose of running a fair trial for PHR services. Each computing device 18 associated with a respective PHR service can correctly interpret the data model of the PHR data both in terms of data format and data semantics. In one embodiment, transactions prompted by a user associated with one of the user devices 12 are published to the network 16 (e.g., a PHR trial ecosystem) to indicate a user's desire to participate in a PHR ecosystem trial. The computing devices 18 maintain a distributed ledger, which may include one or more of a log of previously executed contracts, product price information, which party is linked to which product, transfer price information, etc. for all parties. The distributed ledger (e.g., blockchain) may also include one or more of assets that may change ownership, an order, and individual items that make up the order. The distributed ledger records the movement of a token asset between each service provider with a timestamp generated when the asset changes hands, resulting in an audit trail of timestamps that are trusted by all of the service providers and used to determine that a fair PHR ecosystem trial is executed. In one embodiment, the distributed ledge maintains a smart contract per PHR ecosystem trial to enforce trial periods per PHR ecosystem member (each PHR service provider) and operate as a level of logical indirection to preserve anonymity between the trial service ecosystem and the user. The oracle device 20 may collect trial duration offers (TDOs) from each of the computing devices 18 (e.g., each of the service providers) to combine into a set of rules, or smart contract, with the rules corresponding to, for instance, trial durations. The oracle device 20 operation is governed by the service providers through consensus and voting rights on how the oracle device 20 should work. The PHR ecosystem trial smart contract is published to the distributed ledger that orchestrates and enforces the trial process.

Figure 2A:
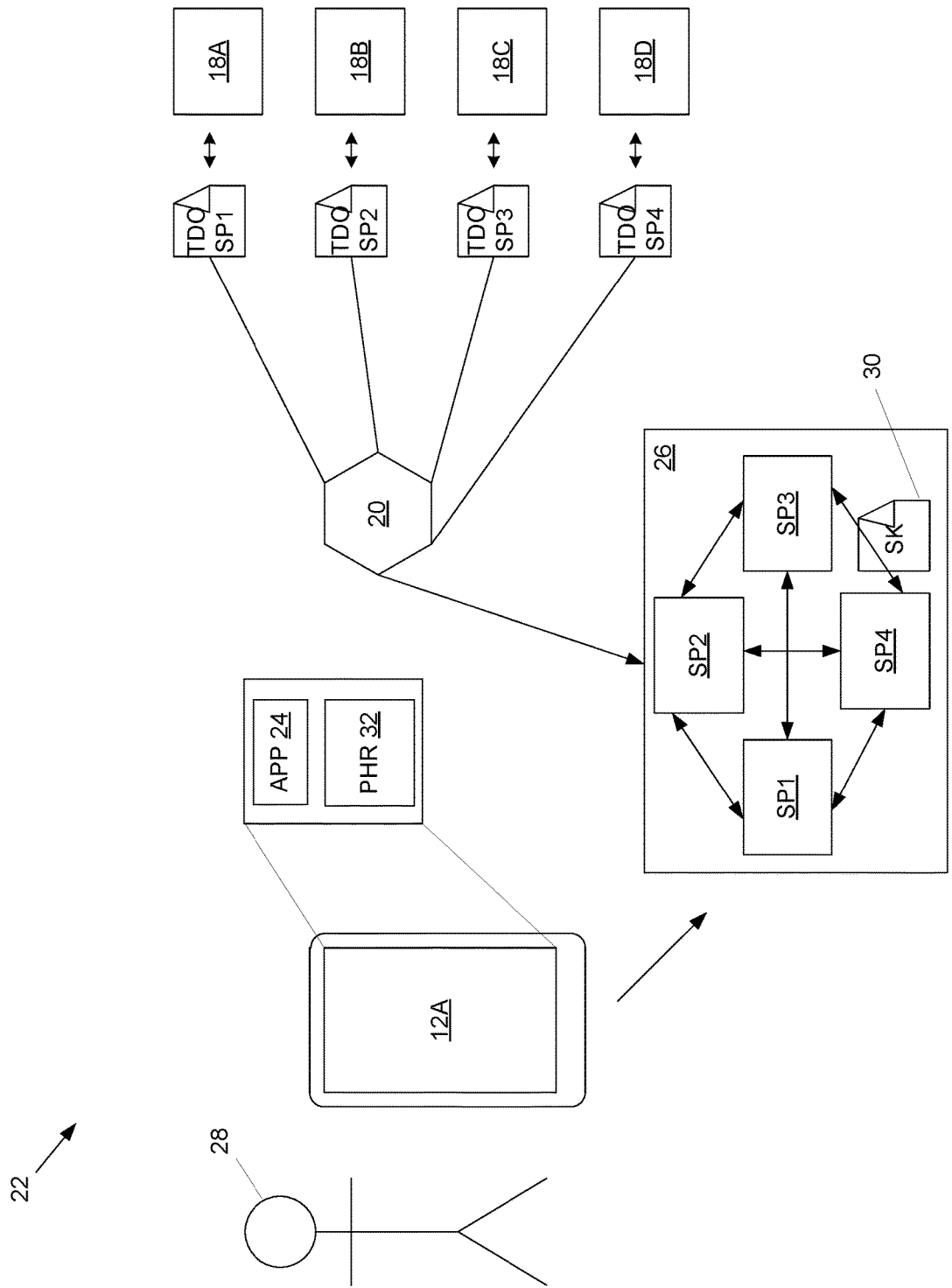
FIG. 2A is a schematic diagram that conceptually illustrates an example PHR ecosystem utilizing a mobile app and a distributed ledger, in accordance with an embodiment of the invention.

Attention is now directed to FIG. 2A, which conceptually illustrates an example PHR ecosystem 22 utilizing a mobile app (APP) 24 and a distributed ledger 26. In general, the example PHR ecosystem 22 is depicted to convey that the distributed ledger 26, when in a settled state after consensus of the rules, is logically in synch between all of the nodes. Though described in the context of PHR trial period services, it should be appreciated by one having ordinary skill in the art in the context of the present disclosure that an ecosystem directed to trial period services of other assets may be implemented in some embodiments, and hence are contemplated to be within the scope of the disclosure. In one embodiment, the PHR ecosystem 22 comprises a user device 12A associated with a user 28 that interacts with a distributed ledger 26, the distributed ledger 26 based on consensus among plural service providers associated with nodes or computing devices 18 (e.g., 18A-18D). In one embodiment, the distributed ledger 26 comprises a public infrastructure for enabling the marketplace, maintaining a set of immutable transactions that can be trusted by all participants (e.g., users, service providers) as a record of intent and actions in this collaborative system. Note that the quantity of PHR service providers is merely illustrative of one example, and that fewer or additional PHR service providers may be used in some embodiments. Also, though the user device 12A is depicted in the form of a smartphone, other types of user devices 12 as described above may be used in some embodiments.

Digressing briefly, and as described above, a current approach to signing up to a PHR service is that a user signs up individually to each service and then initially shares personal information such as name, email address and possibly other sensitive data. Such users often sign-up for the PHR services, which initially sound interesting, but once these services are tried, the users may realize the services are not what they expected or are unhappy with the service for some reason. During sign-up, users are usually asked to provide sensitive, personal information, and their data is collected when using the service. Later, when the user unsubscribes or stops using the service, it is not straightforward (or maybe it is not possible at all) to completely delete the user data from the service provider's (or providers') records.

In contrast, certain embodiments of a PHR ecosystem provide a user the option of operating a trial period in privacy within an ecosystem of competing PHR solutions before deciding if they would like to continue to a full-service sign-up with one of them and share more information with the PHR service provider. For instance, the user may wish to preserve his privacy and not overshare data, yet also wants the convenience of having the trials orchestrated between each PHR service provider. The time spent by the user on each trial period service should be transparent in order to promote fairness in the PHR ecosystem trial as the marketplace is subject to rules that incentivize both users to participate (in terms of convenience and privacy) and ecosystems of PHR service providers to collaborate as it is ultimately to their benefit as they learn what their customer segment really wants. One advantage of this approach is the prevention of oversharing of personal data with trial period service providers whose services the user may never use again. As to benefits for the service providers, service providers may wish to have a way to prove that the service was downloaded on a specific date and by a specific user to protect themselves from giving away more than one free trial of the service, or for other (e.g., legal) reasons. Also, this approach may lead to better conversions of their PHR service for their customer segment. Once a user has decided to commit (subscribe) to a particular PHR service, the user may prove when they started their trial period by providing a receipt to the service provider that indicates when the trial was started by the user. Certain embodiments of a PHR ecosystem achieve this function in a trackable manner using distributed ledger technology. Also, a service provider wants to ensure that the PHR ecosystem trial is fair and the user does not get to experience a trial period service for longer than agreed with other service providers. Using a distributed ledger technology gives control over his or her PHR data to the user, facilitates combinations of different PHR services, while enabling tracking of all transactions.

Referring again to FIG. 2A, the PHR ecosystem 22 uses smart contracts (SK) 30 that can orchestrate a process of moving between different PHR providers to ensure a fair trial period of each service provider. This is possible whilst not sharing personal data of the user 28 with the PHR service providers as the data is stored independently of the PHR service providers and under the control of the user. That is, certain embodiments of a PHR ecosystem 22 provide a solution that enables the users to remain private during the PHR ecosystem trial period whilst allowing them to test the different PHR provider services, until they have decided to commit to using it (e.g., to subscribe to the particular PHR service provider's PHR services). The smart contract 30 enforces the rules of the trial and decides when the trial moves to the next SP based on the agreed trial duration offer. At the end of the trial period among all of the involved service providers, the smart contract 30 checks that all trials were successfully completed and then, in some embodiments, transfers one or any combination of incentives in full to the user 28. The user 28 may then use the incentive as credit for the use of the PHR service they ultimately decide to sign-up and use. Note that incentives as described herein may be provided at one or more instances of time, including prior to the trial period, during, and/or after.

The user device 12A comprises the mobile app 24, which in one embodiment comprises an ecosystem trial app that runs inside a secure mobile app container and runs on the user device 12A. That is, the mobile app 24 comprises a secure mobile app container having an execution environment (e.g., sandboxed) with all of the software dependencies for the downloaded PHR app (e.g., downloaded from the computing device(s) of the corresponding provider). In some embodiments, including for extra security, the secure mobile app container is supported by a trusted execution environment, which is implemented as a secure location inside a processor (e.g., central processing unit or CPU) to ensure that the code is executed as intended. The secure mobile app container prevents user data stored in the secure PHR storage (PHR) 32 from being sent out from the user device 12A. The mobile app 24, implemented as a PHR ecosystem trial app, provides the ability to securely install, execute, and vacate a PHR app as the trial process is orchestrated. It also provides a capability to interact with the distributed ledger 26 to generate the ecosystem trial preferences specified by the user. As explained above, the PHR storage 32 is under full control of the user 28, and each computing device 18 of the PHR services providers is configured to interpret, for instance, the data model and data semantics of the PHR data stored therein. The distributed ledger 26 comprises the smart contract 30, which enforces trial period services per each PHR ecosystem member (service provider).

Figure 2B:
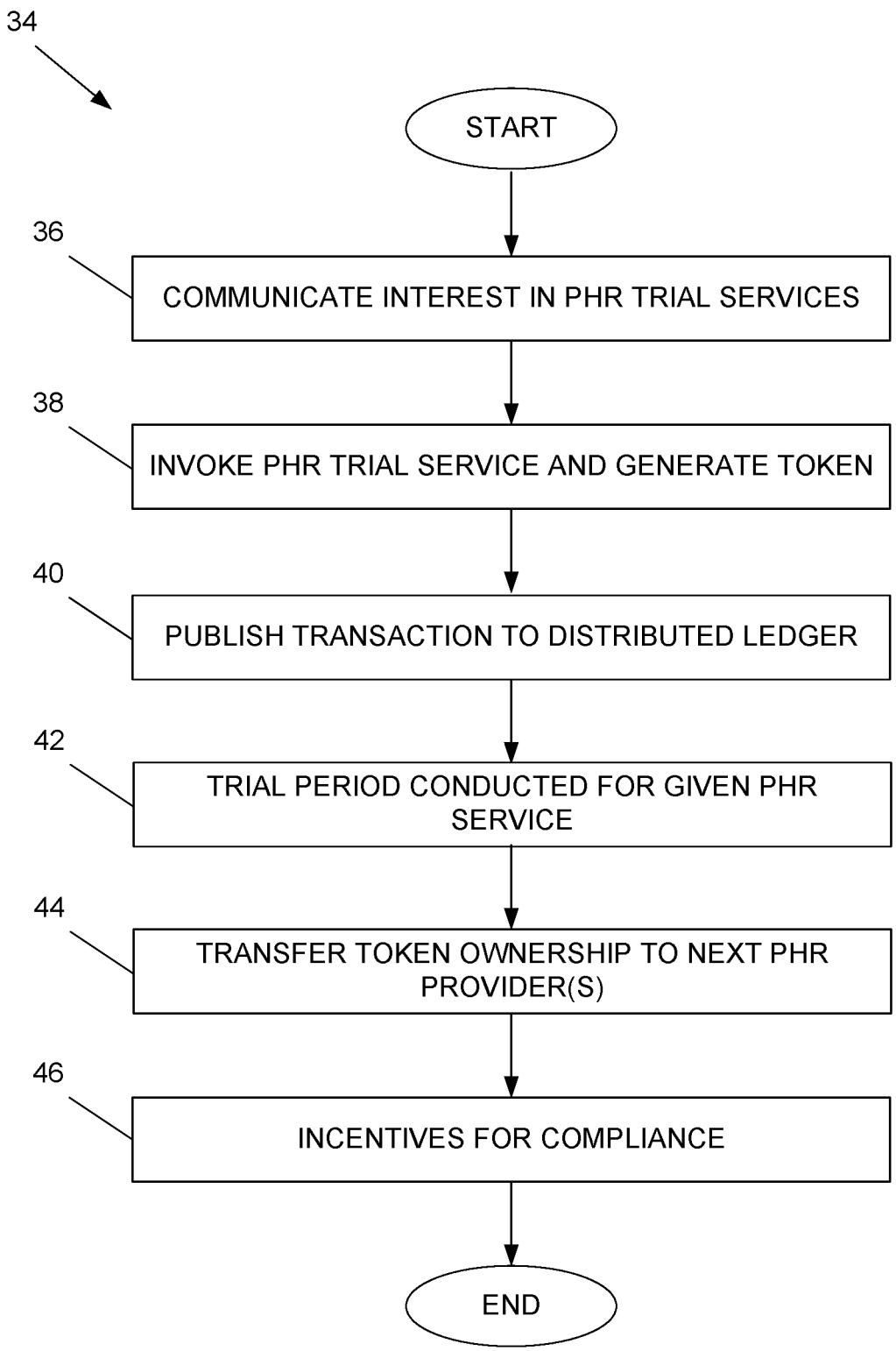
FIG. 2B is a flow diagram that illustrates an example process implemented by the PHR ecosystem of FIG. 2A.

The following is a description, in conjunction with FIGS. 2A and 2B, of an example process 34 implemented by an embodiment of the PHR ecosystem 22. It should be appreciated by one having ordinary skill in the art that variations to the description that follows may be implemented, including steps performed concurrently, in a different order, and/or fewer or additional steps in some embodiments. It is assumed that the user 28 does not yet have a PHR. In this example, PHR services are provided by plural (e.g., four (4)) PHR service providers associated with respective computing devices 18A-18D, though it should be understood that there may be additional computing devices per PHR service provider in some embodiments. The user 28 wishes to be led through a trial of a number of different PHR services to decide which one to ultimately use. The user 28 also wants to do this without sharing their identity (remain anonymous). Assume for this example that the four PHR service providers comprise a set of insurance providers who each offer a PHR service. The user 28 may be considered an individual interested in trialing a PHR service or an authorized individual representing an organization (e.g., hospital) that wishes to trial a PHR service to rollout to a wider customer base. The user 28 may choose their insurance provider based on the PHR service they ultimately choose. In this example, the functionality and capabilities of the PHR drive the selection of the insurer. Referring to FIG. 2B, with continued reference to FIG. 2A, in (36), the user 28 initiates their interest in participating in a PHR ecosystem. For instance, the user 28 through his user device 12A communicates an indication of interest to participate in a PHR ecosystem trial. In (38), the user 28 invokes on his user device 12A the PHR trial service and a unique token is generated from the combination of the user's device (e.g., user device 12A) details and their unique self-sovereign identity ID.

For instance, the mobile app 24 of the user 28 may maintain an identity wallet or module having identity data of the user (e.g., stored on a persistent storage device of the user device 12A, optionally backed-up on another local device or personal backup solution), as opposed to being stored at a central repository. The identity wallet may initially consist of only a self-generated identification number derived from a public key and a corresponding private key used to create a digital signature. In this case, there is nobody or entity with knowledge of this use-device generated identification number, and hence it is self-sovereign. The identification number, along with an identity claim or claims, is used to obtain attestations from relevant authorities. The attested claims can then be used as the identity information. This combination of user device details and the identification number is hashed (or in some embodiments, encrypted using other and/or additional cryptographic methods or formats) and written as a transaction to the public distributed ledger 26 (40) where the transaction receives a timestamp from the ledger and the smart contract 30 is deployed to the distributed ledger 26 to manage the ownership (e.g., possession) of the token. This means that the exact start time of the trial period is recorded. The signing and writing of the transaction means the trial of the PHR service has now officially begun, and each time the service is used, the trial period of the PHR service is checked against the smart contract logic 30 in the public distributed ledger 26. The smart contract logic 30 comprises a set of rules that enforce the trial duration offer (TDO) for each PHR service provider associated with computing devices 18. The oracle device 20 generates the smart contract logic 30 once the user 28 indicates their interest in experiencing the trial based on one or more parameters/criteria. For instance, one parameter may be the number of PHR service providers the user 28 would like to trial. Another parameter may be a total incentive amount the user 28 would like to earn.

The user 28 uses the PHR service for a given PHR service provider (42) up to the end of trial period which includes using their self-sovereign identity to connect with remote devices to store personally collected data from healthcare provider electronic health records (EHRs) (e.g. to pull and store their healthcare data) and/or health data from other sources (e.g., government web sites, health/medical websites, social media, etc.). None of this information is stored with the PHR provider's service. In (44), once the smart contract 30 (note that smart contract and smart contract logic are used herein interchangeably) calculates that the trial period service for a particular PHR service provider is over, the ownership to the token is automatically transferred to the next PHR service provider in the chain. The smart contract checks that all the trial period services are fully complied with and then disburses the incentives from each SP to the user (46) where incentives are offered.

Figure 3:
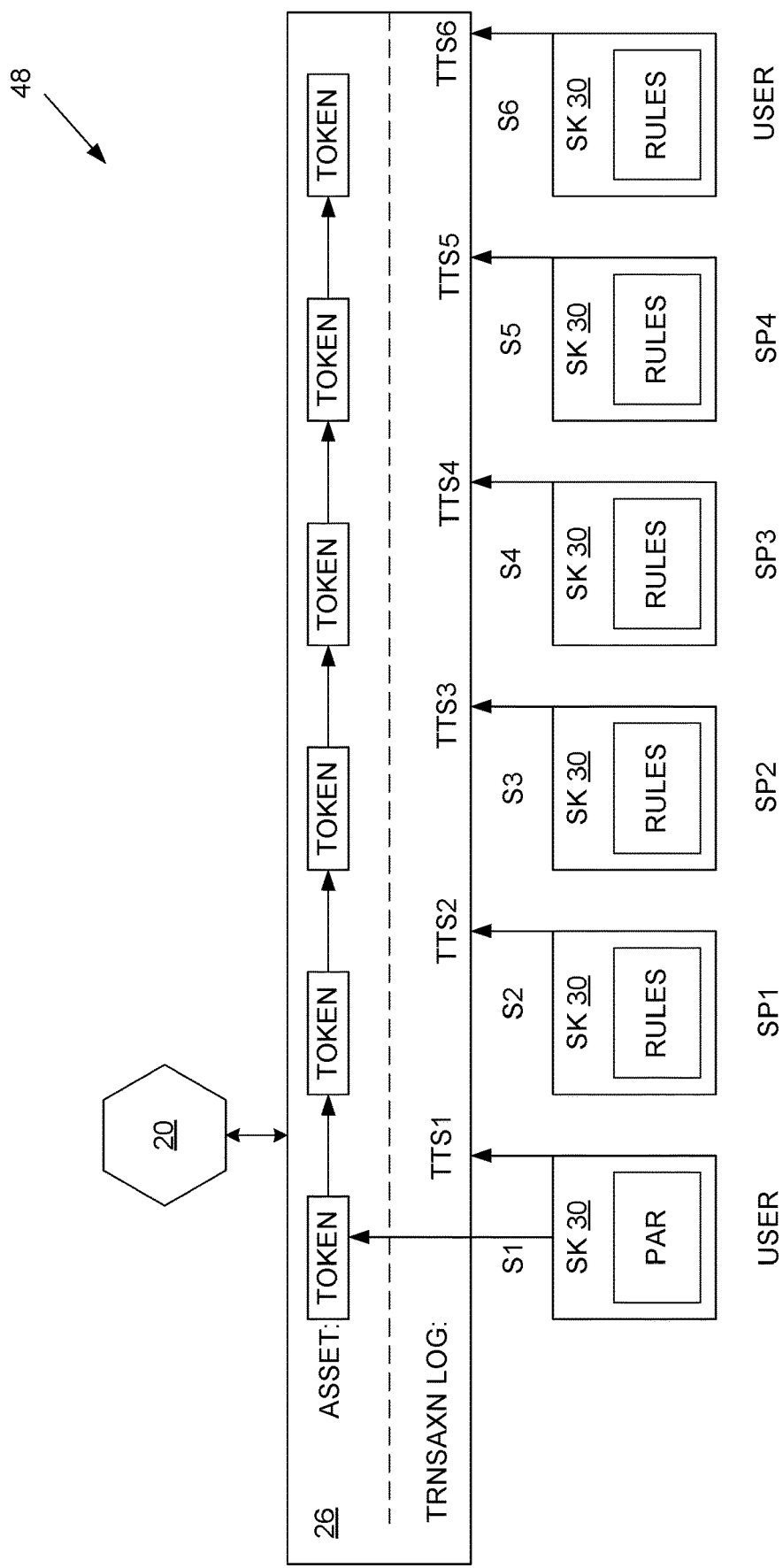
FIG. 3 is a schematic diagram that conceptually illustrates an example method for implementing a trial period in a PHR ecosystem, in accordance with an embodiment of the invention.

FIG. 3 is a schematic diagram that conceptually illustrates an example method 48 for implementing a trial period in the PHR ecosystem 22. In particular, FIG. 3 illustrates some of the steps (S) described above and illustrated in FIGS. 2A and 2B. In the depicted example, the distributed ledger 26 comprises a transaction log that timestamps (TTS) the completion of events performed by the user (e.g., the user device 12A) and further shows the transfer of ownership/possession of the asset (e.g., the token) during the trial period. The smart contract (SK) 30 is shown beneath the distributed ledger 26, and the entity (e.g., user, service provider) associated with the smart contract implementation at the various stages of the trial period is indicated beneath the smart contract 30. Note that SP refers to service provider (e.g., the PHR service provider in this example). In step S1, the user publishes interest in a PHR ecosystem trial and specifies desired parameters (PAR) for the trial period. For instance, in the example depicted in FIG. 2A, the parameters include the number of PHR service providers and the total incentive amount. In some embodiments, other and/or additional parameters may be used. For instance, the criterion or parameters chosen for this example is based on an interest in fairness of the trial among the service providers, and in this case it is measured by proving that the user only spends an agreed amount of time trialing each PHR service. One or more criteria/parameters may be added to provide an added level of sophistication, some of which are described further below. A token is created from a hash of the device identification plus a universal user identifier, and a timestamp (TTS1) transaction is generated. The oracle device 20, as explained above, collects the PHR service provider offers and combines them according to any one or combination of parameters. For instance, the oracle device 20 combines the PHR service providers such that the total incentive amount requested by the user is exceeded by the number of requested service providers or less. Other and/or additional parameters for the combination may be used. The oracle device 20 comprises an automated service created by the ecosystem of the PHR service providers (e.g., in the PHR ecosystem 22). The oracle device 20 matches a user's published desire to participate in a trial with the requirements of the PHR service providers based on trial duration offers (TDOs) and, optionally, incentives. This creates a unique trial ecosystem consisting of selected PHR service providers from a wider pool of service providers. In the case where there may exist more than one equally matching trial ecosystem in the overall pool of service providers, one approach may be to choose just the first one found that matches the user's preferences.

In step S2, during the interaction between the user and the PHR services of SP1, the smart contract 30 performs a logic routine to ensure the rules of the trial period are enforced. For instance, the smart contract 30 determines if the owner of the current token is service provider1 (SP1), and also if the timestamp minus the prior timestamp (TTS1) is greater than the agreed upon trial period time duration offer for SP1 ($TDO_{SP1}$), and if so, a second TTS2 transaction is created and the token is transferred to a next service provider (SP2). In step S3, the user is now interacting with the PHR services of SP2, and in similar fashion, the smart contract logic 30 determines for the owner of the token (e.g., SP2) whether the timestamp minus the prior timestamp (TTS2) exceeds the time duration offer of SP2 ($TDO_{SP2}$), and if so, creates a transaction TTS3 and transfers the token to SP3. In step S4, the user is now interacting with the PHR services of SP3, and in similar fashion, the smart contract logic 30 determines for the owner of the token (e.g., SP3) whether the timestamp minus the prior timestamp (TTS3) exceeds the time duration offer of SP3 ($TDO_{SP3}$), and if so, creates a transaction TTS4 and transfers the token to SP4. In step S5, the user is now interacting with the PHR services of SP4, and similarly, the smart contract logic 30 determines for the owner of the token (e.g., SP4) whether the timestamp minus the prior timestamp (TTS4) exceeds the time duration offer of SP4 ($TDO_{SP4}$), and if so, transfers the token to the user. In step S6, if the user has fulfilled each trial duration as agreed, then the combined incentives offered by the service providers (e.g., SP1-SP4) are disbursed to the user. Note that in some embodiments, there are no incentives.

Figure 4:
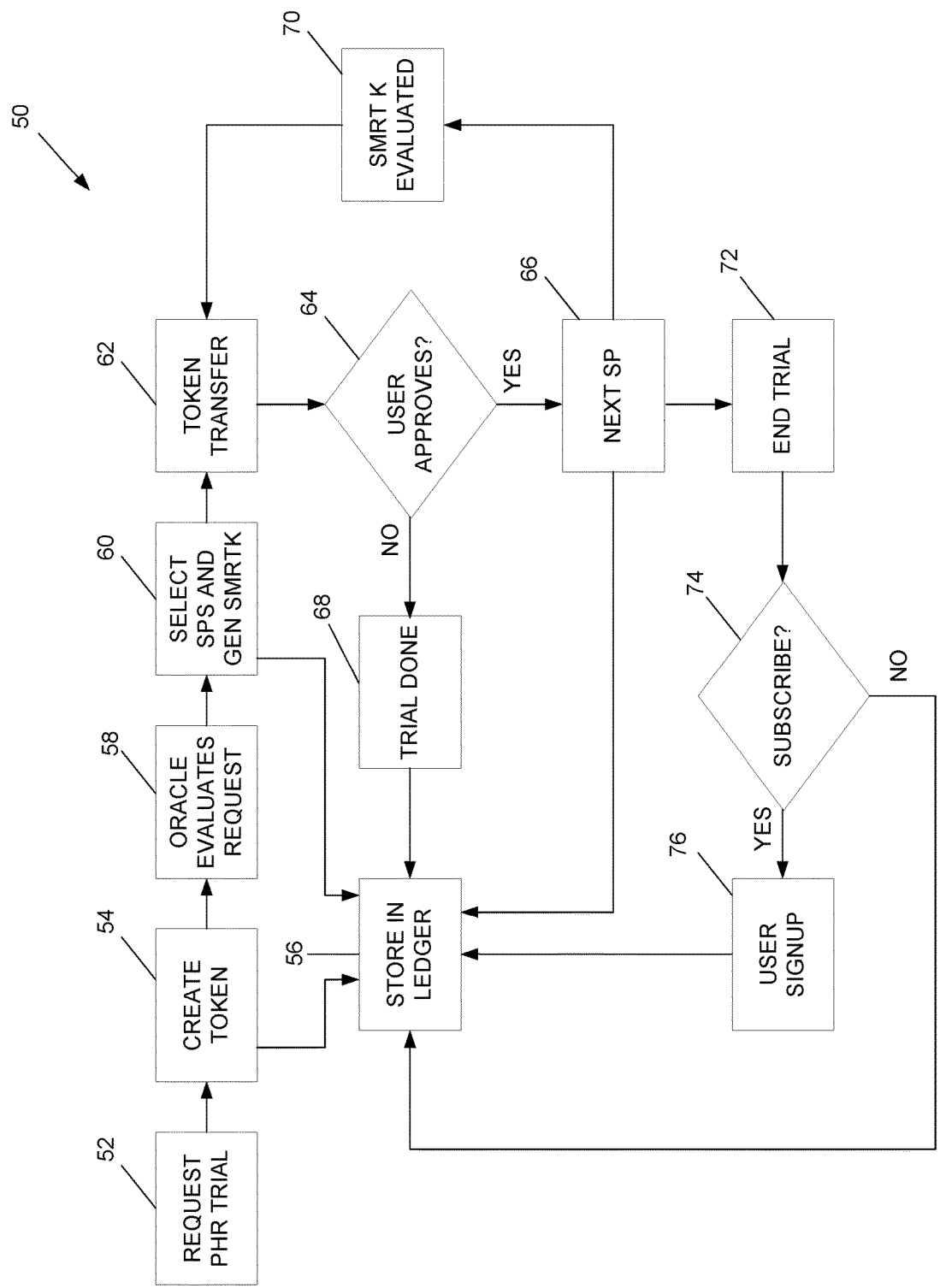
FIG. 4 is a flow diagram that illustrates an example trial process, in accordance with an embodiment of the invention.

FIG. 4 illustrates an embodiment of an example trialing process 50 implemented by the PHR ecosystem 22. In some embodiments, fewer or additional steps in the process 50 may be implemented, and hence are contemplated to be within the scope of the disclosure. The process 50 illustrated in FIG. 4 comprises steps that may be used with the process/methods 34 and 48 in FIGS. 2B and 3. With continued reference to FIGS. 2A-3, and referring to FIG. 4, in (52), the user 28 requests a PHR trial (via the user device 12A). A token is created based on the request (54), and stored in the distributed ledger 26 (56). Based on the request of the user, the oracle device 20 evaluates the request (58), which includes determining a group of PHR service providers that match the parameters of the user request. If such a group matching the user's request can be found, the process 50 may proceed. In case no suitable PHR service providers (SPs) can be found, this information is stored in the distributed ledger 26 (not shown in the FIG. 4), and the user 28 may be asked for a new request or to modify the current request. At this stage the oracle device 20 may offer suggestions to the user 28 in some embodiments. Assuming a match may be found, the PHR service providers matching the user parameters are selected for trialing, and a smart contract 30 is generated (60) and stored in the distributed ledger 26 (56). In (62), the token is transferred to a first PHR service provider (SP1), and the user decides whether to approve the token transfer (64). Notably, the user 28 is in control of this stage in the process 50, making a determination whether he wishes to try the first PHP service provider. If approved, the trial period with the scheduled first PHR service provider begins (66). If not approved, the trial finishes (e.g., is done) (68) and the transactions are recorded in the ledger (56). In embodiments where incentives are offered, all the user 28 loses are any incentives that he may have earned if he had completed the trial according to the smart contact 30. Assuming the user tries the first PHR service provider (66), during the interaction with the selected PHR trial service, the smart contract 30 is evaluated (70). For instance, the smart contract 30 evaluates whether the trial period has ended (see, e.g., the rules in FIG. 3), and if the TDO for the particular PHR service expires, the token is transferred (serially) to the next PHR service provider from the group of PHR service providers (62). After the trial period (for all PHR service providers) is finished (72), the user 28 is given the option to sign up (formally) to one of the PHR services that he has tested (74). If the user 28 wants to sign up (76), then in the case of available incentives, the incentives earned (by adhering to the smart contact 30) may be also used (e.g., as a discount to the subscription to the selected PHR service, as a credit, etc.). If the user decides not to sign up, this information is stored in the distributed ledger 26 (56), and in the case of incentives, the incentives may be lost or not lost depending on the nature of the smart contact 30.

Notably, for certain embodiments of a PHR ecosystem (e.g., PHR ecosystem 22), distinctions may be readily drawn from conventional trial periods. For instance, a user does not need to worry about searching for service provider specifications. Rather, a user merely provides high level information or parameters for his request (e.g., I want to find insurance providers that can provide the best care for heart failure patients like me). A benefit to this approach is evident in today's world where there is a plethora of choices that require considerable investigation for users to find a suitable service. Further, and viewing the ecosystem in a broader context (e.g., beyond PHR services), unlike conventional services for insurance, mobile phone, or energy providers that have websites to facilitate the choice among many options for the user, in certain embodiments of an ecosystem as disclosed herein, it is the service providers themselves that provide the marketplace with a common set of rules without the need for an intermediary (with the possibility for receipt of incentives). Such trial ecosystem service providers come to an agreement on the rules, and they can all then verify that the rules were followed without the need for an intermediary.

Figure 5:
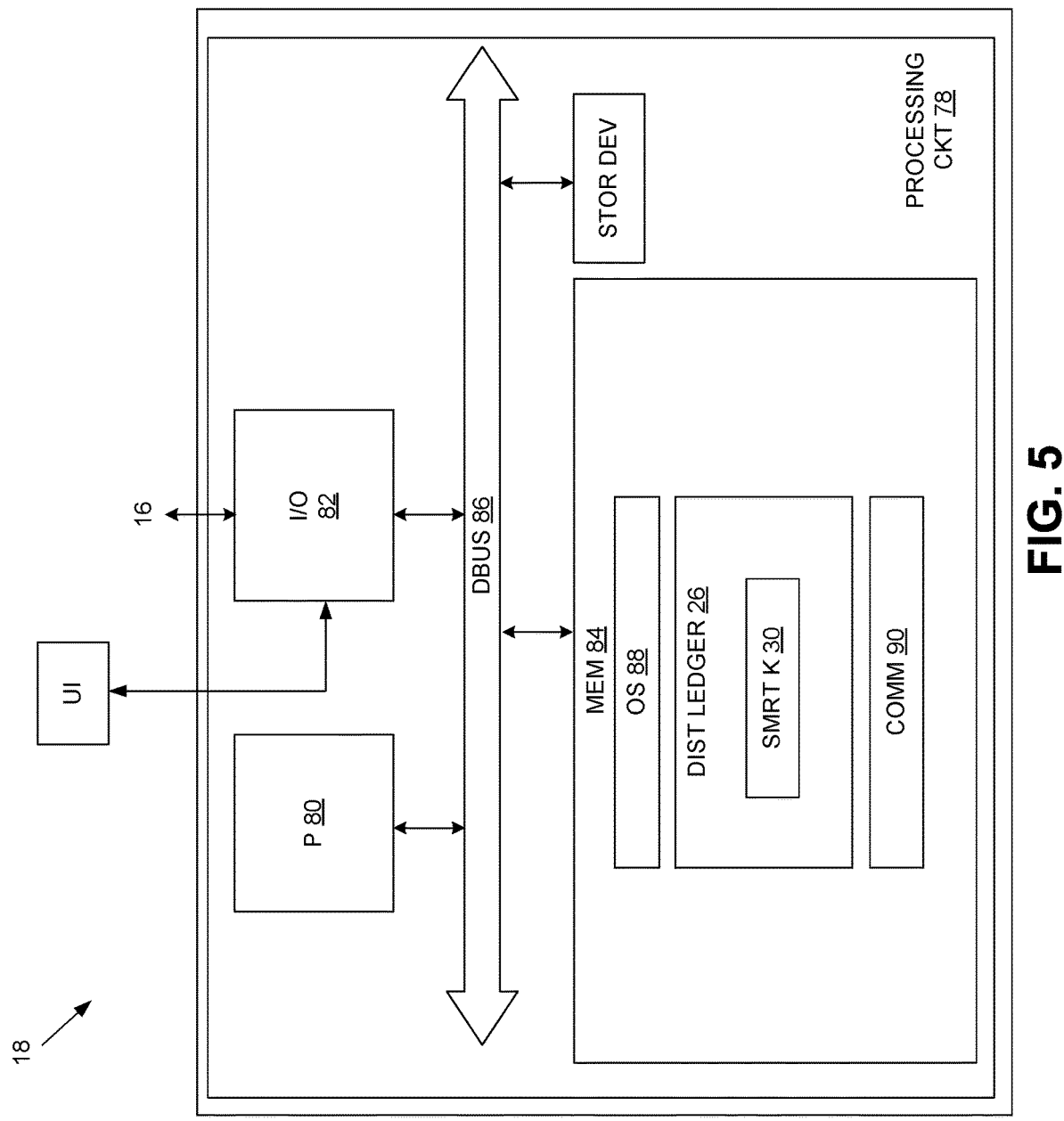
FIG. 5 is a block diagram that illustrates an example computing device serving as a node in the PHR ecosystem of FIG. 2A, in accordance with an embodiment of the invention.

Having described an embodiment of a PHR ecosystem 22 and methods 34, 48, and 50, attention is directed to FIG. 5, which illustrates an embodiment of an example computing device 18. The computing device 18 may be embodied as an application server, computer, among other computing devices. One having ordinary skill in the art should appreciate in the context of the present disclosure that the example computing device 18 is merely illustrative of one embodiment, and that some embodiments of computing devices may comprise fewer or additional components, and/or some of the functionality associated with the various components depicted in FIG. 5 may be combined, or further distributed among additional modules or computing devices, in some embodiments. The computing device 18 is depicted in this example as a computer system, such as one providing a function of a node in a distributed ledger network (e.g., blockchain peer-to-peer network) 16. It should be appreciated that certain well-known components of computer systems are omitted here to avoid obfuscating relevant features of the computing device 18. In one embodiment, the computing device 18 comprises a processing circuit 78 (PROCESSING CKT) that comprises one or more processors, such as processor 80 (P), input/output (I/O) interface(s) 82 (I/O), one or more user interfaces (UI), which may include one or more of a keyboard, mouse, microphone, speaker, etc.), and memory 84 (MEM), all coupled to one or more data busses, such as data bus 86 (DBUS). In some embodiments, the user interfaces may be coupled directly to the data bus 86. The memory 84 may include any one or a combination of volatile memory elements (e.g., random-access memory RAM, such as DRAM, and SRAM, etc.) and nonvolatile memory elements (e.g., ROM, Flash, solid state, EPROM, EEPROM, hard drive, tape, CDROM, etc.). The memory 84 may store a native operating system, one or more native applications, emulation systems, or emulated applications for any of a variety of operating systems and/or emulated hardware platforms, emulated operating systems, etc. In some embodiments, a separate storage device (STOR DEV) may be coupled to the data bus 86 or as a network-connected device (or devices) via the I/O interfaces 82 and the network 16. The storage device may be embodied as persistent memory (e.g., optical, magnetic, and/or semiconductor memory and associated drives), and in some embodiments, may be used to store data depicted as stored in memory 84, including the distributed ledger 26 and/or the smart contract 30.

In the embodiment depicted in FIG. 4, the memory 84 comprises an operating system 88 (OS), and application software that includes a distributed ledger 26, which in turn includes smart contract (SMRT K) logic 30, and communications software (COMM) 90. Note that the memory 84 may also be referred to herein as a non-transitory, computer readable storage medium. The distributed ledger 26 and smart contract logic 30 have been described above, and hence description of the same here is omitted for brevity. The communications software 90 comprises functionality to communicate with the user device 12 and the oracle device 20, and may include connectivity logic for communications with an Ethereum network among other networks.

Execution of the distributed ledger 26, the smart contract logic 30, and the communications software 90 may be implemented by the processor 80 under the management and/or control of the operating system 88. The processor 80 may be embodied as a custom-made or commercially available processor, a central processing unit (CPU) or an auxiliary processor among several processors, a semiconductor based microprocessor (in the form of a microchip), a macroprocessor, one or more application specific integrated circuits (ASICs), a plurality of suitably configured digital logic gates, and/or other well-known electrical configurations comprising discrete elements both individually and in various combinations to coordinate the overall operation of the computing device 18.

The I/O interfaces 82 comprise hardware and/or software to provide one or more interfaces to devices coupled to the network 16, as well as to other devices such as the user interface. In other words, the I/O interfaces 82 may comprise any number of interfaces for the input and output of signals (e.g., analog or digital data) for conveyance of information (e.g., data) over various networks and according to various protocols and/or standards. The user interfaces may include a keyboard, mouse, microphone, immersive head set, etc., which enable input and/or output by an administrator or other user.

When certain embodiments of the computing device 18 are implemented at least in part with software (including firmware), as depicted in FIG. 5, it should be noted that the software (e.g., the distributed ledger 26, the smart contract logic 30, and the communications software 90) can be stored on a variety of non-transitory computer-readable (storage) medium for use by, or in connection with, a variety of computer-related systems or methods. In the context of this document, a computer-readable medium may comprise an electronic, magnetic, optical, or other physical device or apparatus that may contain or store a computer program (e.g., executable code or instructions) for use by or in connection with a computer-related system or method. The software may be embedded in a variety of computer-readable mediums for use by, or in connection with, an instruction execution system, apparatus, or device, such as a computer-based system, processor-containing system, or other system that can fetch the instructions from the instruction execution system, apparatus, or device and execute the instructions.

When certain embodiments of the computing device 18 are implemented at least in part with hardware, such functionality may be implemented with any or a combination of the following technologies, which are all well-known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), relays, contactors, etc.

Figure 6:
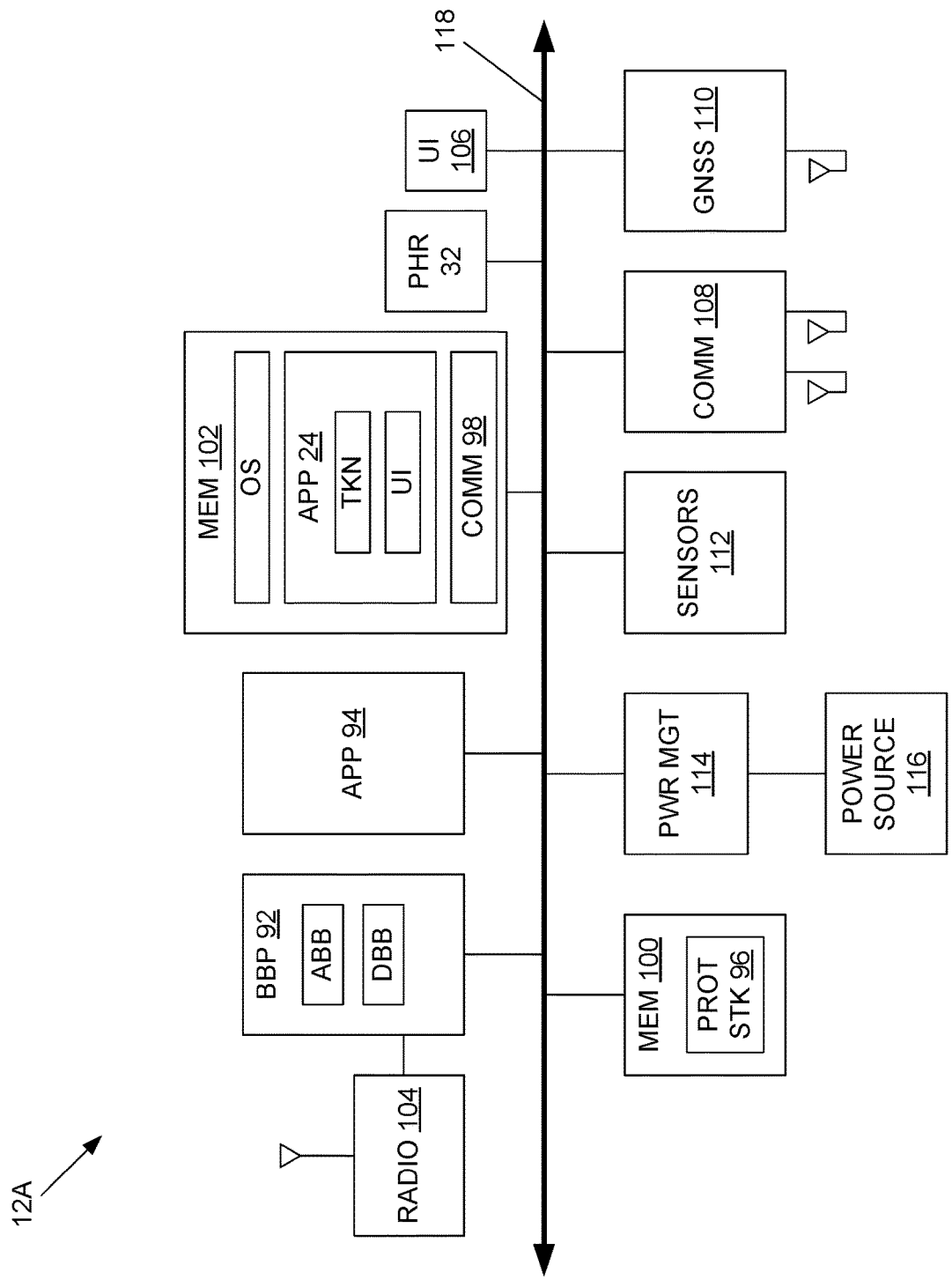
FIG. 6 is a block diagram that illustrates an example mobile device serving as a user device in the PHR ecosystem of FIG. 2A, in accordance with an embodiment of the invention.

Referring now to FIG. 6, shown is an example user device 12A. In the depicted example, the user device 12A is embodied as a smartphone, though in some embodiments, other types of devices may be used, such as a laptop, notebook, tablet, professional devices, etc. comprising a similar hardware architecture to that described in association with the computing device 18 and a similar software architecture to that described below in the memory of the user device 12A. It should be appreciated by one having ordinary skill in the art that the logical block diagram depicted in FIG. 6 and described below is one example, and that other designs may be used in some embodiments. The user device 12A comprises at least two different processors, including a baseband processor (BBP) 92 and an application processor (APP) 94. As is known, the baseband processor 92 primarily handles baseband communication-related tasks and the application processor 94 generally handles inputs and outputs and all applications other than those directly related to baseband processing. The baseband processor 92 comprises a dedicated processor for deploying functionality associated with a protocol stack (PROT STK) 96, such as a GSM (Global System for Mobile communications) protocol stack, among other functions. The application processor 94 comprises a multi-core processor for running applications, including the mobile app 24 and communications software 98, as described further below. The baseband processor 92 and application processor 94 have respective associated memory (e.g., MEM) 100, 102, including random access memory (RAM), Flash memory, etc., and peripherals, and a running clock. The user device 12A further includes secure memory/storage (PHR) 32. In some embodiments, the PHR 32 may be implemented using a trusted execution environment. Note that, though depicted as residing in memory 102, all or a portion of the mobile app 24 and/or communications software 98 may be stored in one or any combination of memory 100, 102, and/or 32, or reside in other memory.

More particularly, the baseband processor 92 may deploy functionality of the protocol stack 96 to enable the user device 12A to access one or a plurality of wireless network technologies, including WCDMA (Wideband Code Division Multiple Access), CDMA (Code Division Multiple Access), EDGE (Enhanced Data Rates for GSM Evolution), GPRS (General Packet Radio Service), broadband (e.g., 3G, 4G, 5G), streaming services (e.g., LoRa), Zigbee (e.g., based on IEEE 802.15.4), Bluetooth, Wi-Fi (Wireless Fidelity, such as based on IEEE 802.11), and/or LTE (Long Term Evolution), among variations thereof and/or other telecommunication protocols, standards, and/or specifications. The baseband processor 92 manages radio communications and control functions, including signal modulation, radio frequency shifting, and encoding. The baseband processor 92 comprises, or may be coupled to, a radio (e.g., RF front end) 104 and/or a GSM modem, and analog and digital baseband circuitry (ABB, DBB, respectively in FIG. 6). The radio 104 comprises one or more antennas, a transceiver, and a power amplifier to enable the receiving and transmitting of signals of a plurality of different frequencies, enabling access to the wireless/cellular network 14 (FIG. 1), and hence the communication of user data, measurements, associated contexts, and/or feedback information. The analog baseband circuitry is coupled to the radio 104 and provides an interface between the analog and digital domains of the GSM modem. The analog baseband circuitry comprises circuitry including an analog-to-digital converter (ADC) and digital-to-analog converter (DAC), as well as control and power management/distribution components and an audio codec to process analog and/or digital signals received indirectly via the application processor 94 or directly from the smartphone user interface (UI) 106 (e.g., microphone, speaker, earpiece, ring tone, vibrator circuits, display screen, etc.). The ADC digitizes any analog signals for processing by the digital baseband circuitry. The digital baseband circuitry deploys the functionality of one or more levels of the GSM protocol stack (e.g., Layer 1, Layer 2, etc.), and comprises a microcontroller (e.g., microcontroller unit or MCU, also referred to herein as a processor) and a digital signal processor (DSP, also referred to herein as a processor) that communicate over a shared memory interface (the memory comprising data and control information and parameters that instruct the actions to be taken on the data processed by the application processor 94). The MCU may be embodied as a RISC (reduced instruction set computer) machine that runs a real-time operating system (RTIOS), with cores having a plurality of peripherals (e.g., circuitry packaged as integrated circuits) such as RTC (real-time clock), SPI (serial peripheral interface), I2C (inter-integrated circuit), UARTs (Universal Asynchronous Receiver/Transmitter), devices based on IrDA (Infrared Data Association), SD/MMC (Secure Digital/Multimedia Cards) card controller, keypad scan controller, and USB devices, GPRS crypto module, TDMA (Time Division Multiple Access), smart card reader interface (e.g., for the one or more SIM (Subscriber Identity Module) cards), timers, and among others. For receive-side functionality, the MCU instructs the DSP to receive, for instance, in-phase/quadrature (I/Q) samples from the analog baseband circuitry and perform detection, demodulation, and decoding with reporting back to the MCU. For transmit-side functionality, the MCU presents transmittable data and auxiliary information to the DSP, which encodes the data and provides to the analog baseband circuitry (e.g., converted to analog signals by the DAC).

The application processor 94 operates under control of an operating system (OS) that enables the implementation of one or a plurality of applications, including the mobile app 24 and the communications software 98. The application processor 94 may be embodied as a System on a Chip (SOC). The application processor 94 and/or the baseband processor 92 may execute the communications software 98 and mobile app 24. The mobile app 24 comprises a secure mobile app container that prevents any user data stored in memory (e.g., PHR storage 32) from being sent out from the user device 12A. The mobile app 24 provides functionality to securely install, execute, and vacate a PHR app from PHR service providers. The mobile app 24 further comprises token generation functionality (TKN) that hashes user device parameters and/or universal identifiers to obtain a unique token. The mobile app 24 further comprises user interface functionality (UI) that operates in cooperation with the user interface 106 to enable the user 28 to interact with the PHR services. For instance, the user interface module comprises an application that interacts with the smart contract 30 to enforce the rules of the trial. The PHR service from each PHR service provider runs inside the mobile app 24 (e.g., trial ecosystem app) and presents (e.g., displays) the user interface (e.g., graphical user interface or GUI) of a specific PHR service provider during the trial turn of that PHR service provider. When a trial expires, the user 28 receives a notification indicating that the current trial has completed. The data collected from that trial is saved to the user controlled storage 32 and the next step in the ecosystem trial is initiated. As explained above, this process continues until all service providers have had their trial or the user terminates the trial services of the ecosystem. The mobile app 24 also, in cooperation with the radio 104 and/or a communications interface 108, enables interactions with the distributed ledger 26 to generate the ecosystem trial preferences. Notably, the functionality of the mobile app 24 prevents the user identity from ever being exposed to the PHR service providers during the trial period. Only after the user 28 decides to sign up (e.g., subscribe) to a particular PHR service provider may his identity be exposed (e.g., assuming this is a requirement by the PHR service provider for permitting a subscription).

The application processor 94 generally comprises a processor core (Advanced RISC Machine or ARM), and further comprises or may be coupled to multimedia modules (for decoding/encoding pictures, video, and/or audio), a graphics processing unit (GPU), communications interfaces (COMM) 108, and device interfaces. In one embodiment, the communication interfaces 108 may include wireless interfaces, including a Bluetooth (BT) (and/or Zigbee in some embodiments) module that enable wireless communications with one or more devices of the environment 10 (FIG. 1), including the other user devices 12 (e.g., 12C), and a Wi-Fi module for interfacing with a local 802.11 network, according to corresponding software in the communications software 98. In some embodiments, the radio 104 may be considered a communications interface. The application processor 94 further comprises, or is coupled to, a global navigation satellite systems (GNSS) transceiver or receiver (GNSS) 110 for enabling access to a satellite network to, for instance, provide coordinate location services. In some embodiments, the GNSS receiver 110, in association with GNSS functionality in the communications software 98, collects contextual data (time and location data, including location coordinates and altitude), which may be used for storage with measured data.

In one embodiment, the user device 12A comprises sensors 112, which may include one or any combination of a PPG sensor, an ECG sensor, and a motion sensor(s) (e.g., an accelerometer, inertial sensors, including a gyroscope). For instance, the PPG sensor may be embodied as an optical sensor (e.g., a charged coupled device (CCD) or a complementary metal-oxide semiconductor (CMOS) optical sensor), which is used to detect various physiological parameters of a user, including blood pressure or breathing rate based on remote photoplethysmography (PPG). The sensors 112 may also include other types of sensors, including electromyograph (EMG) sensors, impedance sensors, skin temperature sensors, etc.

The device interfaces coupled to the application processor 94 may include the user interface 106, including a display screen. The display screen may be embodied in one of several available technologies, including LCD or Liquid Crystal Display (or variants thereof, such as Thin Film Transistor (TFT) LCD, In Plane Switching (IPS) LCD)), light-emitting diode (LED)-based technology, such as organic LED (OLED), Active-Matrix OLED (AMOLED), or retina or haptic-based technology. Other user interfaces 106 may include a keypad, microphone, speaker (e.g., to audibly present feedback), ear piece connector, I/O interfaces (e.g., USB (Universal Serial Bus)), SD/MMC card, lighting (e.g., to provide a visualization of the monitoring conditions, including via different colored LEDs or different illumination patterns of the LEDs), or a tactile device (e.g., vibration motor to provide tactile feedback), among other peripherals. In some embodiments, the user interface 106 may include virtual and/or augmented reality functionality.

Also included is a power management device 114 that controls and manages operations of a power source (e.g., battery) 116. The components described above and/or depicted in FIG. 6 share data over one or more busses, and in the depicted example, via data bus 118. It should be appreciated by one having ordinary skill in the art, in the context of the present disclosure, that variations to the above example description of the user device 12A may be deployed in some embodiments to achieve similar functionality.

In the depicted embodiment, the application processor 94 runs the app 24 and communications software 98, though in some embodiments, the baseband processor 92 or a combination of both processors 92, 94 may run the app 24 and communications software 98.

The communications software 98 and/or protocol stack 96 comprises executable code (instructions) to enable the communications interface 108 and/or the radio 104 to communicate with other devices of the environment 10 (FIG. 1). Communications may be achieved according to one or more communications technologies, including broadband or streaming technologies, GSM, LTE, CDMA, WCDMA, Wi-Fi, 802.11, Bluetooth, NFC, etc.).

Note that variations to the above-described embodiments are contemplated to be within the scope of the disclosure. For instance, after a user decides upon a PHR service provider (e.g., after the trial period is completed), the user subscribes to the PHR service provider and may share health data with the PHR service provider. Assume that the user subscribes to a PHR service 1 ($SP_1$). In conjunction with this subscription, assume a PHR database is created (e.g., Database1 or DB1). Note that other data structures may be used in some embodiments. Later, the user may decide to enroll in another PHR service, $SP_2$. At this stage, the user may have to contend with making certain choices regarding sharing personal data collected by $SP_1$, and sharing information about Database 1. TABLE 1 below illustrates some example conditions (states of data sharing) and implications arising from this example.

TABLE 1

| DB1 Information Sharing | User Data Sharing | Implications |
|---|---|---|
| Not allowed | Not allowed | $SP_2$ defines and uses its own database (Database 2), and only the data collected by $SP_2$ service is stored in the Database 2. |
| Approved | Not allowed | $SP_2$ uses the same database structure, allowing easy integration of |

TABLE 1-continued

| DB1 Information Sharing | User Data Sharing | Implications |
|---|---|---|
| | | Database 1 and Database 2 if necessary at the later stages. |
| Not allowed | Allowed | Note that this case is highly unlikely, because from the users perspective it is difficult to imagine why a personal data would be shared, and database data would not be shared. (In one case, this may be due to legal reasons for instance) $SP_2$ defines its own database structure. User data collected by $SP_1$ is accessible from Database 1. |
| Allowed | Allowed | $SP_2$ adopts the structure of Database 1 and data collected by $SP_1$ is used. |

It is noted that $SP_1$ stores the data in Database 1 and $SP_2$ in Database 2. If the user and $SP_1$ allow the sharing of database structure information with $SP_2$, combining both databases (if necessary in the future) should be easy. If $SP_1$ and the user allow user data to be shared with $SP_2$, the service provided by $SP_2$ can potentially be better or with different functionality. From the perspective of the user, one advantage of allowing multiple service providers to interact may include a better and wider range of services. From the perspective of the service providers, an advantage of interacting with each other may be that they can focus on specific functionalities and services, hence improving the quality and decreasing the cost.

Further, it is assumed above that the user interacts with each of the various PHR services during the trial period for the entire TDO period, as enforced by the smart contracts. However, in some embodiments, a smart contract may be implemented where the user has some control over the TDO based on their ability to skip to the next trial before the agreed TDO has elapsed, which in the case where incentives are offered, may result in the user not receiving the full incentive for that specific trial.

Also, the description above discloses the determining of a group of PHR service providers by an oracle device based on the requirements of the user, and then the trialing process commencing according to interactions with each of the service providers in that group. However, in some embodiments, the PHR service providers may be dynamically changed by the oracle device based on the user's actions in the current trial. This may be done on the basis that additional intelligence has been gathered on user preferences and/or needs.

In some embodiments, selection of PHR service providers may be optimized. In other words, rather than the oracle device merely matching the user's trial preferences to the subset of PHR service providers that match, the oracle device may approach the search and selection process as more of an optimization problem where the number of trials are maximized or minimized to reach the users stated incentive goal. For example, the user may express a desire to minimize the number of PHR service providers yet still meet their incentivization goal. As another example, the user may not mind how many PHR service providers are involved in the trial, but they would like to maximize their incentives. In another example that represents an intermediate to the prior two examples, the user can specify the number (+/−some flexibility) and incentives (+/−flexibility).

In some embodiments, where the user does not yet state a preference for the number of PHR service providers or incentive goal, the oracle device may interact with the user to decide on the trial ecosystem. In this case, the oracle device may discover the user's preferences with the aim of finding a trial ecosystem, where the preferences go beyond specifying just the number of PHR service providers and the incentive goal.

In some embodiments, there may be more flexibility in the order of trials. For instance, the user may switch at will between PHR service providers in an ecosystem trial but only up until a specific trial period for a given PHR service provider is exhausted. By doing so, biases that may result based on being either the first or last PHR service provider in the trial are removed or mitigated.

The use of a distributed ledger has certain benefits over centralized control from a third ($3^{rd}$) party service. For instance, a common solution for identity management is a central repository. Often a commercial third party owns and controls a repository of many people's identities. The customer enters their personal details into some kind of form to submit their data and uploads supporting evidence. Whomever needs this can access this data (with consent from the user), and can systematically pull this data into their own systems. If details change, the customer updates it once, and can push the change to the connected entities. This of course means that they need to trust the $3^{rd}$ party to not process or share their data for purposes beyond those agreed. A solution using anything other than a distributed ledger solution raises trust issues. For example, a third party may provide a resembling service without a ledger but then all the trial ecosystem partners need to trust the third party and possibly pay them a fee when their user converts. For instance, it may be that just because the ecosystem gets a new user who wants to run an ecosystem trial, the third party charges a fee to the ecosystem providers. Such issues do not arise when the intermediary is removed (e.g., when using a distributed ledger solution).

One or more benefits that may arise from the use of certain embodiments of a PHR ecosystem for a patient with a disease (e.g., with epilepsy) may be that the patient can focus on taking care of himself, and attending to the needs of the disease, instead of searching around for service providers and worrying if he is receiving the best care (because he may have missed some service providers in his own search). That is, the patient attends to the disease in an optimal and efficient manner (e.g., in terms of time and money). The patient may also being rewarded for trying different service providers, which is an extra reward. One or more benefits of certain embodiments of a PHR ecosystem for the service providers, other than the trust issue discussed above, includes the fact that they can focus on proving their service in the best possible manner (e.g., best care for the patient), instead of worrying about marketing and getting access to the patients. In addition, by being able to collect anonymous patient data (e.g., if approved by the user) during the trials, they have better means/tools to improve their services. In other words, it is a new way to acquire users and to learn from user choices. Another benefit for the service providers is that certain embodiments of a PHR ecosystem enable them to share information among each other.

Figure 7:
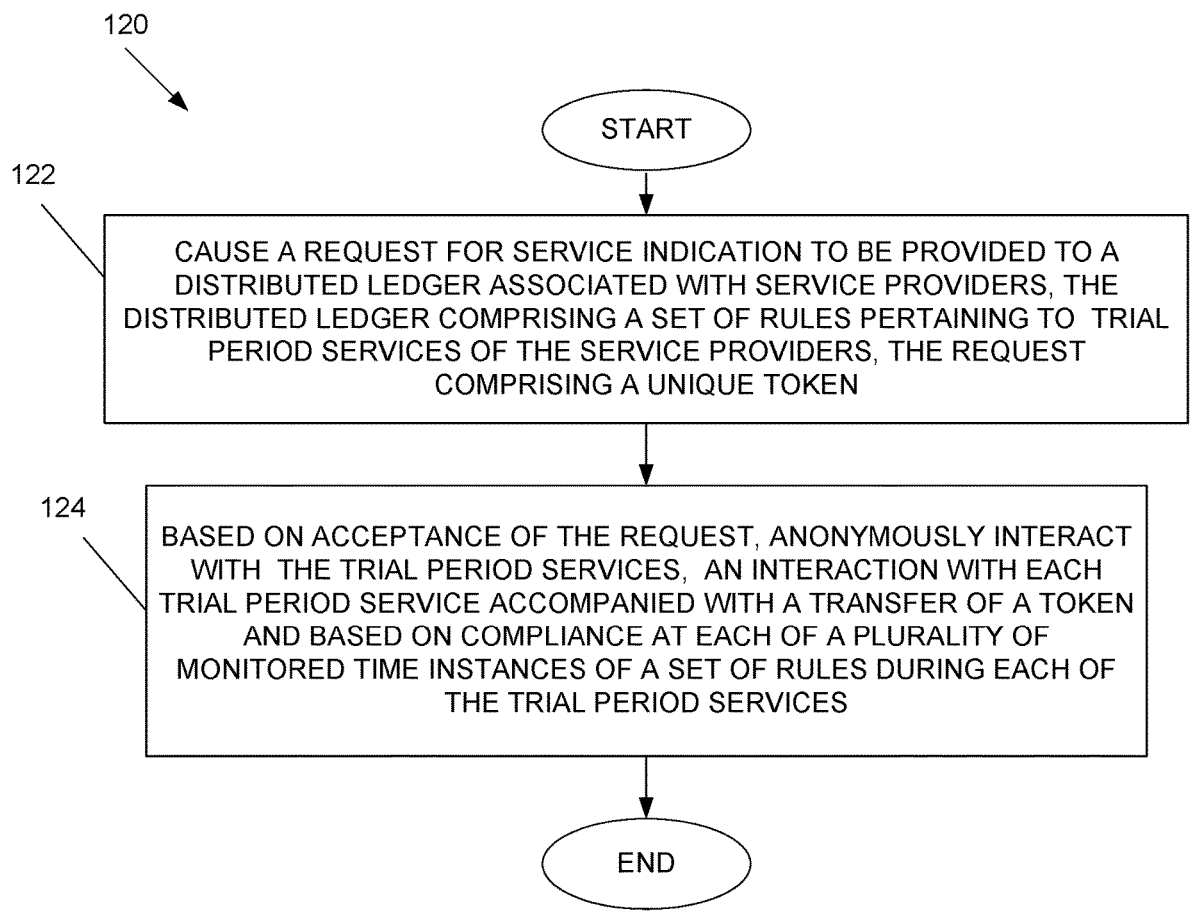
FIG. 7 is a flow diagram that illustrates an example method for implementing a trial period in a PHR ecosystem, in accordance with an embodiment of the invention.

Having described certain embodiments of a PHR ecosystem, it should be appreciated that one embodiment of an example method for implementing a trial period in a PHR ecosystem, depicted in FIG. 7 and denoted as method 120, which is shown bounded by a start and end, comprises causing a request for service indication to be provided to a distributed ledger associated with service providers, the distributed ledger comprising a set of rules pertaining to trial period services provided by the service providers, the request comprising a unique token (122); and based on acceptance of the request, anonymously interacting with the trial period services, an interaction with each trial period service accompanied with a transfer of a token and based on compliance at each of a plurality of monitored time instances of a set of rules during each of the trial period services, each interaction with trial period services occurring while retaining exclusive storage of the data of the user in the memory, each of the trial period services associated with a respective one of the service providers (124).

Any process descriptions or blocks in flow diagrams should be understood as representing modules, segments, or portions of code which include one or more executable instructions for implementing specific logical functions or steps in the process, and alternate implementations are included within the scope of the embodiments in which functions may be executed out of order from that shown or discussed, including substantially concurrently or in reverse order, depending on the functionality involved, as would be understood by those reasonably skilled in the art of the present disclosure. In some embodiments, one or more steps may be omitted, or further steps may be added.

In one embodiment, a user device is disclosed, comprising: a communications interface configured to enable communications with service providers, the service providers providing trial period services comprising a trial period of a defined type; a memory comprising an app that provides exclusive control of access to data of a user stored therein; and one or more processors configured by the app to: cause a request for service indication to be provided to a distributed ledger associated with the service providers, the distributed ledger comprising a set of rules pertaining to the trial period services, the request comprising a unique token; and based on acceptance of the request, anonymously interact with the trial period services, an interaction with each trial period service accompanied with a transfer of a token and based on compliance at each of a plurality of monitored time instances of a set of rules during each of the trial period services, each interaction with the trial period services occurring while retaining exclusive storage of the data of the user in the memory, each of the trial period services associated with a respective one of the service providers.

In one embodiment, the prior user device, wherein the one or more processors are configured by the app to generate the token based on a combination of characteristics of the user device and a unique self-sovereign identity.

In one embodiment, any one of the prior user devices, wherein the one or more processors are configured by the app to configure the token in a cryptographic format and provide the request as a transaction acceptable to the distributed ledger.

In one embodiment, any one of the prior user devices, wherein the set of rules correspond to smart contract logic at the distributed ledger.

In one embodiment, any one of the prior user devices, wherein the set of rules correspond to a trial duration offer for each of the service providers.

In one embodiment, any one of the prior user devices, wherein the one or more processors are configured by the app to retrieve and store in the memory health data from one or more health data sources.

In one embodiment, any one of the prior user devices, wherein the one or more processors are further configured to receive any one or a combination of incentives associated with the trial period services.

In one embodiment, any one of the prior user devices, wherein the one or more processors are configured to receive the one or combination of incentives at one or more instances of time, the one or more instances of time including before the interaction, during the interaction, and after the interaction.

In one embodiment, any one of the prior user devices, further comprising a user interface, wherein the one or more processors are configured by the app to receive an indication from logic associated with the distributed ledger when each trial period service is completed.

In one embodiment, any one of the prior user devices, wherein the one or more processors are configured by the app to prevent a transfer of the token and interactions when the trial period services is terminated.

In one embodiment, any one of the prior user devices, wherein the one or more processors are further configured by the app to communicate a first subscription to one of the service providers after completion of the trial period services and a second subscription with another of the service providers after interacting with the one of the service providers according to the first subscription, the one or more processors further configured by the app to control sharing of the user data between the one of the service providers and the another of the service providers.

In one embodiment, any one of the prior user devices, wherein the one or more processors are configured by the app to switch among the plural trial period services before completing a prescribed trial period duration for each trial period service as long as a total duration prescribed for each of the trial period services has been met.

In one embodiment, any one of the prior user devices, wherein the trial period services collectively correspond to a trial period for a personal health record service.

In one embodiment, a system is disclosed, comprising: plural service providers, each configured to provide a trial period service collectively comprising a trial period of a defined type; and a computing device comprising a distributed ledger communicatively coupled to the plural service providers, wherein the distributed ledger comprises a set of rules, the distributed ledger configured to: receive a transaction from a user device, the transaction providing an indication of an anonymous user associated with the user device of participating in the trial period, the transaction comprising a token uniquely associated with the user device; and transfer the token to a first service provider of the plural service providers and then subsequent service providers of the plural service providers based on, respectively, acceptance of the transaction and user interaction with the respective trial period services after the transaction, wherein the distributed ledger enforces compliance with, for each trial period service of a respective one of the plural service providers in possession of the token, a trial period service duration established according to the set of rules while maintaining anonymity of the user.

In one embodiment, the prior system, wherein the distributed ledger is further configured to record a receipt of the transaction using a time stamp.

In one embodiment, any one of the prior systems, further comprising a third party device comprising an oracle, wherein the oracle configures the set of rules based on one or more parameters, the oracle matching requirements of the user to requirements of the plural service providers in the set of rules, wherein the set of rules comprise a smart contract.

In one embodiment, any one of the prior systems, further comprising a third party device comprising an oracle, wherein the oracle is configured to perform one or any combination of the following: dynamically change selection of the plural service providers based on interactions of the user during the trial period with at least one of the service providers; optimize a number of trial period services based on a goal of the user; and iteratively interact with the user to determine user preferences.

In one embodiment, any one of the prior systems, further comprising a secure storage configured to securely store data of the user and prevent access by any of the plural service providers at least during each trial period service.

In one embodiment, any one of the prior systems, wherein the distributed ledger is configured to communicate an indication to the user device when a trial period service for one of the plural service providers is over, the distributed ledger further configured to automatically transfer the token to a subsequent service provider among the plural service providers to provide a next trial period service associated with the subsequent service provider.

In one embodiment, any one of the prior systems, further comprising a data structure that stores user data upon termination of the trial period according to compliance with the set of rules and subscription by the user with a service of the defined type provided by one of the plural service providers, wherein responsive to a user request to switch to another one of the service providers, the distributed ledger is further configured to determine whether the same or a different data structure is used and determine a state of data sharing based on user input.

In one embodiment, a computer-implemented method comprising steps to perform any of the functions of any one of the preceding user device or system.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. For instance, though emphasis is placed on PHR trial services, certain embodiment as disclosed herein may be used for any services that collect and make use of the collected data, including applications related to healthcare, storing and processing medical data, applications related to lifestyle, storing and processing daily activity and social media data, or applications related to combination of both. Note that various combinations of the disclosed embodiments may be used, and hence reference to an embodiment or one embodiment is not meant to exclude features from that embodiment from use with features from other embodiments. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical medium or solid-state medium supplied together with or as part of other hardware, but may also be distributed in other forms. Any reference signs in the claims should be not construed as limiting the scope.

At least the following is claimed:

1. A user device, comprising:
a communications interface configured to enable communications with service providers, the service providers providing trial period services comprising a trial period of a defined type;
a memory comprising an app that provides exclusive control of access to data of a user stored therein; and
one or more processors configured by the app to:
cause a request for service indication to be provided to a distributed ledger associated with the service providers, the distributed ledger comprising a set of rules pertaining to the trial period services, the set of rules enforcing the trial period services and ensuring anonymity of a user of the user device interacting with the trial period services, the request comprising a unique token; and
based on acceptance of the request, anonymously interact with the trial period services, an interaction with each trial period service accompanied with a transfer of the unique token and based on compliance at each of a plurality of monitored time instances of the set of rules during each of the trial period services, each interaction with the trial period services occurring while retaining exclusive storage of the data of the user in the memory, each of the trial period services associated with a respective one of the service providers.

2. The user device of claim 1, wherein the one or more processors are configured by the app to generate the unique token based on a combination of characteristics of the user device and a unique self-sovereign identity.

3. The user device of claim 2, wherein the one or more processors are configured by the app to configure the unique token in a cryptographic format and provide the request as a transaction acceptable to the distributed ledger.

4. The user device of claim 1, wherein the set of rules correspond to smart contract logic at the distributed ledger.

5. The user device of claim 1, wherein the set of rules correspond to a trial duration offer for each of the service providers.

6. The user device of claim 1, wherein the one or more processors are configured by the app to retrieve and store in the memory health data from one or more health data sources.

7. The user device of claim 1, wherein the one or more processors are further configured to receive any one or a combination of incentives associated with the trial period services.

8. The user device of claim 7, wherein the one or more processors are configured to receive the one or combination of incentives at one or more instances of time, the one or more instances of time including before the interaction, during the interaction, and after the interaction.

9. The user device of claim 1, further comprising a user interface, wherein the one or more processors are configured by the app to receive an indication from logic associated with the distributed ledger when each trial period service is completed.

10. The user device of claim 1, wherein the one or more processors are configured by the app to prevent a transfer of the unique token and interactions when the trial period services is terminated.

11. The user device of claim 1, wherein the one or more processors are further configured by the app to communicate a first subscription to one of the service providers after completion of the trial period services and a second subscription with another of the service providers after interacting with the one of the service providers according to the first subscription, the one or more processors further configured by the app to control sharing of the user data between the one of the service providers and the another of the service providers.

12. The user device of claim 1, wherein the one or more processors are configured by the app to switch among the plural trial period services before completing a prescribed trial period duration for each trial period service as long as a total duration prescribed for each of the trial period services has been met.

13. The user device of claim 1, wherein the trial period services collectively correspond to a trial period for a personal health record service.

14. A system, comprising:
plural service providers, each configured to provide a trial period service collectively comprising a trial period of a defined type; and
a computing device comprising:
at least one processor operatively connected to a memory, the at least one processor configured to cause a request for service indication to be provided to a distributed ledger communicatively coupled to the plural service providers, wherein the distributed ledger comprises a set of rules enforcing the trial period services and ensuring anonymity of a user of the user device interacting with the trial period services, the distributed ledger configured to:
receive a transaction from a user device, the transaction providing an indication of an anonymous user associated with the user device of participating in the trial period, the transaction comprising a token uniquely associated with the user device; and
transfer the token to a first service provider of the plural service providers and then subsequent service providers of the plural service providers based on, respectively, acceptance of the transaction and user interaction with the respective trial period services after the transaction, wherein the distributed ledger enforces compliance with, for each trial period service of a respective one of the plural service providers in possession of the token, a trial period service duration established according to the set of rules while maintaining anonymity of the user.

15. The system of claim 14, wherein the distributed ledger is further configured to record a receipt of the transaction using a time stamp.

16. The system of claim 14, further comprising a third party device comprising an oracle, wherein the oracle configures the set of rules based on one or more parameters, the oracle matching requirements of the user to requirements of the plural service providers in the set of rules, wherein the set of rules comprise a smart contract.

17. The system of claim 14, further comprising a third party device comprising an oracle, wherein the oracle is configured to perform one or any combination of the following: dynamically change selection of the plural service providers based on interactions of the user during the trial period with at least one of the service providers; optimize a number of trial period services based on a goal of the user; and iteratively interact with the user to determine user preferences.

18. The system of claim 14, further comprising a secure storage configured to securely store data of the user and prevent access by any of the plural service providers at least during each trial period service.

19. The system of claim 14, wherein the distributed ledger is configured to communicate an indication to the user device when a trial period service for one of the plural service providers is over, the distributed ledger further configured to automatically transfer the token to a subsequent service provider among the plural service providers to provide a next trial period service associated with the subsequent service provider.

20. The system of claim 14, further comprising a data structure that stores user data upon termination of the trial period according to compliance with the set of rules and subscription by the user with a service of the defined type provided by one of the plural service providers, wherein responsive to a user request to switch to another one of the service providers, the distributed ledger is further configured to determine whether the same or a different data structure is used and determine a state of data sharing based on user input.

* * * * *